(12) United States Patent
Sogaro

(10) Patent No.: US 6,547,101 B1
(45) Date of Patent: Apr. 15, 2003

(54) MULTI-CHAMBERED AMPOULE FOR DISPENSING A MIXTURE COMPRISING SEVERAL SUBSTANCES

(75) Inventor: Alberto C. Sogaro, Kronberg (DE)

(73) Assignee: Dentaco Dental Industrie und Marketing GmbH, Bad Homburg (DE)

( * ) Notice: Subject to any disclaimer, the term of this patent is extended or adjusted under 35 U.S.C. 154(b) by 0 days.

(21) Appl. No.: 09/869,400

(22) PCT Filed: Nov. 2, 2000

(86) PCT No.: PCT/EP00/10778

§ 371 (c)(1),
(2), (4) Date: Aug. 3, 2001

(87) PCT Pub. No.: WO01/32242

PCT Pub. Date: May 10, 2001

(30) Foreign Application Priority Data

Nov. 3, 1999 (DE) .................................... 299 19 291 U

(51) Int. Cl.[7] .................................................. B67D 5/52
(52) U.S. Cl. .................... 222/137; 222/82; 222/145.1; 222/327; 222/386
(58) Field of Search .............................. 222/137, 145.1, 222/327, 82, 566, 545, 386

(56) References Cited

U.S. PATENT DOCUMENTS

| | | | |
|---|---|---|---|
| 2,168,686 A | 8/1939 | Saffir | 128/218 |
| 3,572,336 A | 3/1971 | Hershberg | 128/218 |
| 4,303,069 A | 12/1981 | Cohen | 128/218 |
| 4,610,666 A | 9/1986 | Pizzino | 604/191 |
| 5,020,694 A * | 6/1991 | Pettengill | 222/137 |
| 5,335,827 A * | 8/1994 | Gentile | 222/137 |
| 5,881,921 A * | 3/1999 | Seager et al. | 222/137 |
| 6,352,177 B1 * | 3/2002 | Bublewitz et al. | 222/137 |

FOREIGN PATENT DOCUMENTS

| | | |
|---|---|---|
| FR | 2 070 358 | 9/1971 |
| WO | WO 99/17833 | 4/1999 |

* cited by examiner

*Primary Examiner*—Gene Mancene
*Assistant Examiner*—Melvin A. Cartagena
(74) *Attorney, Agent, or Firm*—Quarles & Brady LLP

(57) ABSTRACT

A multi-chambered ampoule for dispensing a mixture of substances comprising: an oblong container (10) having at least two cylindrical chambers (12, 14) which extend in the axial direction from the rear end to the front end of the container, a respective piston (22, 24) which can be slidingly inserted into each chamber in an axial direction, creating a seal with respect to the inner wall of the chamber, and a housing (30) comprising a front section (32) which surrounds a discharge channel (34) and a rear section (36) which is adjacent to the front section, containing an inner chamber (38) formed therein into which the container can be inserted in such a way that the front end of the container defines a mixing chamber (33) inside the housing, leading into a discharge channel and provides a tight closure. In a ready-to-use state, the openings at the rear end of the chambers are closed by pistons and the openings at the front end of the chambers being sealed by a sealing means (40). A substance is contained in each of the closed chambers.

15 Claims, 3 Drawing Sheets

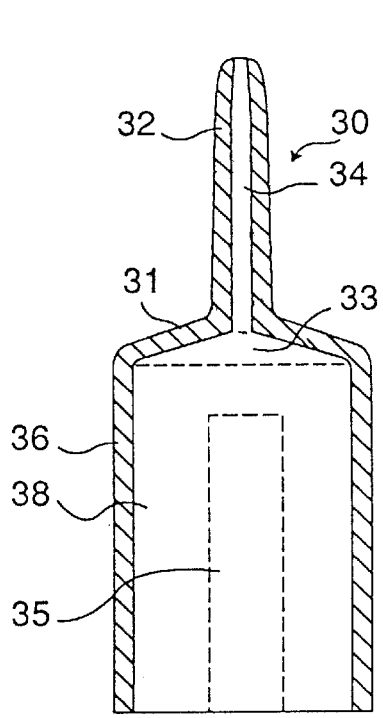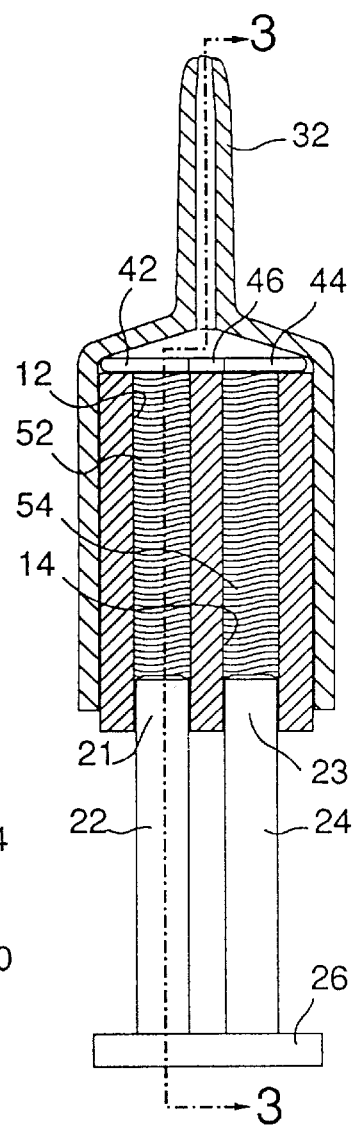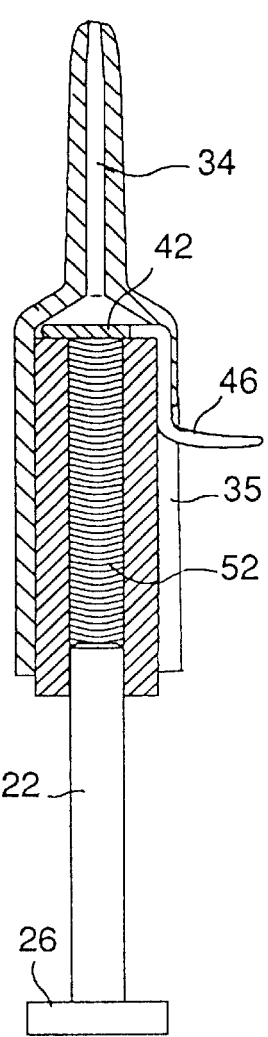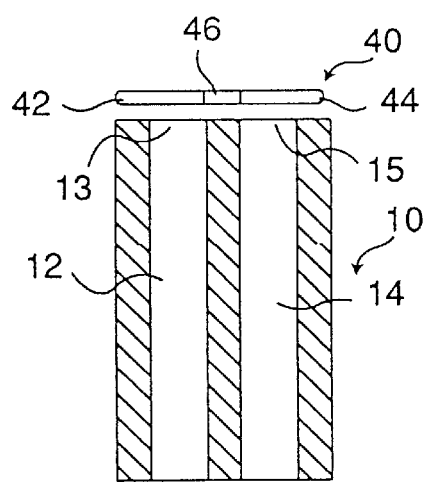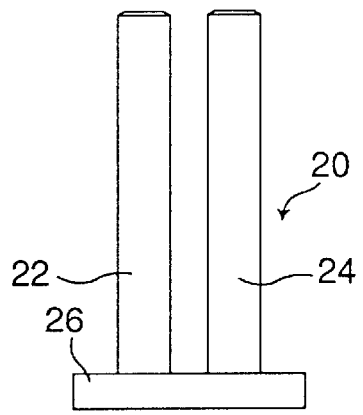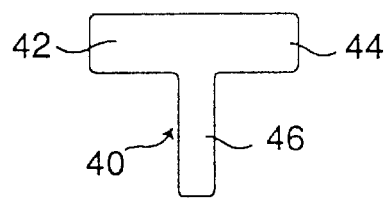

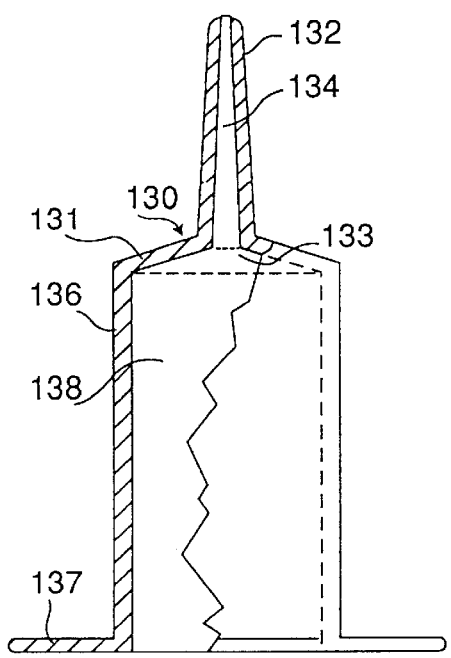
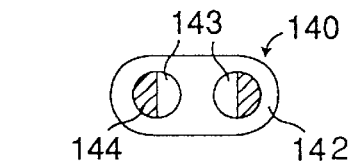
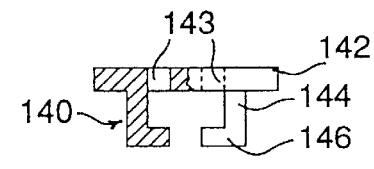
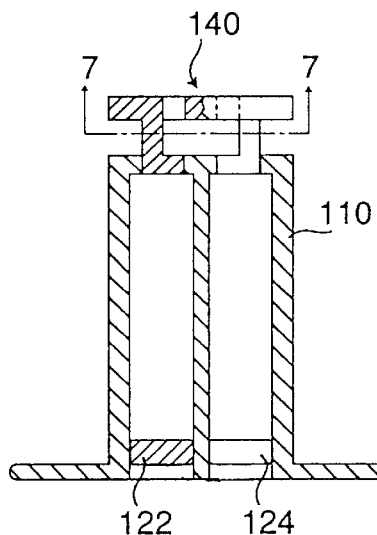
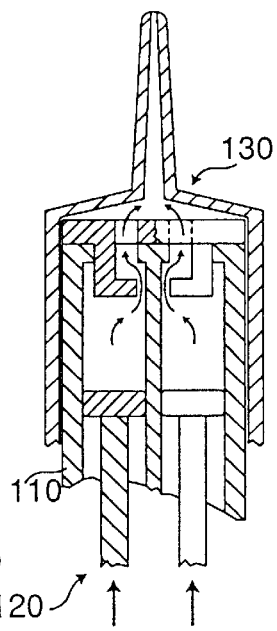
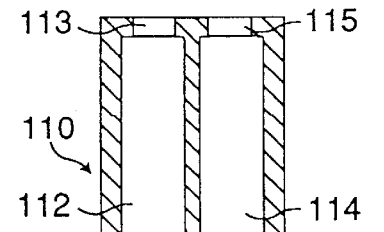
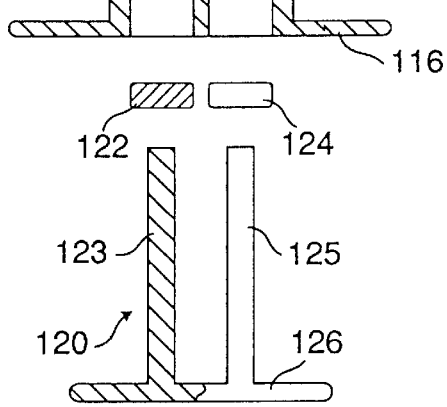
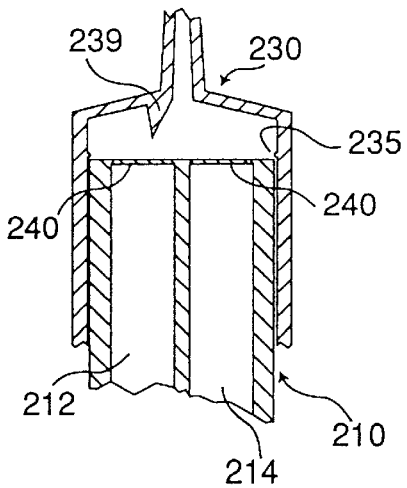

MULTI-CHAMBERED AMPOULE FOR DISPENSING A MIXTURE COMPRISING SEVERAL SUBSTANCES

BACKGROUND OF THE INVENTION

The invention relates to a multi-chamber ampoule for dispensing a mixture comprising several substances.

In the fields of medicine and cosmetics, and in other fields as well, it is frequently necessary for a multi-component product to store the different components separately from one another and just mix them with one another immediately prior to application. Furthermore, it is frequently necessary or at least desirable to store the separate components as tightly sealed as possible.

It is known from EP 0 090 413 A2 to store at least two liquid, fluid, or semi-fluid substances to be mixed during application in separate cartridges which are combined to a unit of several cartridges arranged parallel to one another. The cartridges are made from a soft plastic foil and have an opening at their front end only from which the substance stored in the cartridge can exit. The front end of the cartridge usually tapers into a cone-shaped tip with its discharge opening being closed with a cap. In order to put it into use a unit comprising e.g. two cartridges is inserted into a device provided with a slidable double piston by means of which it is possible to act on the two cartridges. Before activating the double piston the two sealing caps are removed and a common mixing device is mounted onto the tubular exit sections of the two cartridges. The mixing device is provided with two inlet channels and a common exit channel which is in contact with the two inlet channels inside of the mixing device. The entire arrangement of cartridges and means for squeezing out the cartridges and mixing the substances forced out is designed comparatively complicated and cannot easily be operated.

A principally very similar dosing and mixing device is known from EP 0 313 519 A1. Here, two separate cartridges are inserted into a device, which is provided with an automated squeezing unit made from two piston rods being connected to one another. A holding mechanism for the cartridges to be inserted is provided in the housing of the device. Next to said holding mechanism, a mixing device is provided having a mixing chamber into which a mixing means extends which is exchangeable together with the cartridges. Here, the mixing chambers are also connected to the cartridges by means of two inlet channels in the form of two connecting ducts. For this purpose, each cartridge has a narrowing exit end, which is to be tightly connected to the connecting duct when inserting the cartridges into the device. On their exiting end, the cartridges are provided with a valve-like seal which breaks under pressure when the squeezing-out unit is initially put into operation. Alternatively, a tube-shaped coupling part with a sloped ring-shaped blade is provided at the cartridge side end of each connecting duct said blade severing the membrane provided at the exit end of the cartridge when the cartridges are inserted into the device. At the opposite end, the cartridges are sealed with a tear-off lid which is removed prior to the cartridges being inserted into the device. Subsequently, the end of the cartridges facing the squeezing unit is solely sealed by a piston-type element slidingly arranged in the cartridge and insertable therein. This dosing and mixing arrangement is complicatedly constructed, as well, and cannot be operated with ease.

Furthermore, a multitude of syringe fittings has been suggested allowing to dispense mixed substances from ampoules inserted into the syringe fittings. Here, on their exit or discharge side the cartridges are generally provided with a membrane being pierced by hollow needles when operated, which hollow needles mouth into a common hollow exit needle via respective connecting channels. Additionally, the connecting channels are sometimes provided with valves in order to allow a securely sealed transfer of the reacting agents into the common exiting needle. This is referred to in WO 92/10425, U.S. Pat. Nos. 5,314,412, 5,599,312.

In U.S. Pat. No. 5,542,934 the hollow piercing needles mouth into a chamber where the substances mix, and are formed by a cap bolted onto the housing of the cartridges. In AT 366 916 the two syringe bodies are inserted into a common holding arrangement. The cones of the syringe bodies extend into insertable cones of a collecting head. Inside of the collecting head, a separate feed channel leads from each cone to a cone head provided at the collecting head and having a hollow needle. AT 400 675 B describes a syringe fitting in which the syringe body is connected via a connecting piece to form a non-dismountable syringe unit in the shape of a plate into which a piston unit is inserted. Additionally, a dispensing unit that can be mounted onto the syringe unit is provided. The dispensing unit is attached to said syringe unit after removal of the cap-like seal. On its backside, the syringe unit is sealed by movable piston plugs. These plugs are provided with snapping or locking connecting means to the front ends of the piston rods. After the distribution unit is attached, the cones of the syringe bodies mouth into corresponding cone-shaped recesses, which lead into separate channels. The channels mouth into a conventional mixing canule which is attached to the dispensing piece.

BRIEF SUMMARY OF THE INVENTION

It is an object of the invention to provide a multi-chamber ampoule for dispensing a mixture comprising several substances, which ampoule is designed as simple as possible and easily to be operated.

This object is achieved by the subject matter of claim 1 and 10, respectively. Preferred developments of the invention are defined in the subclaims. The multi-chamber ampoule designed according to the invention has the advantage of not requiring any separate devices for dispensing and mixing the substances. Moreover, the dispensing and mixing means are integrated in the proper multi-chamber ampoule and serve additional functions therein. The pistons remaining in the chambers, for example, serve to seal the rear openings of the chambers storing the substances and, in a preferred embodiment, these pistons form the front ends of a one-piece piston unit which does not require any separate piston plugs to be provided additionally which, again, would require a separate piston rod unit in order to shift the plugs. Simultaneously, the mixing device forms the housing for receiving the container provided with the chambers and said housing seals, cooperating with the container, the mixing chamber with respect to undesired leaks. Thus, sealing caps that would have to be removed and dispensing units to be subsequently attached are not required. On the one hand, the requirement for the operator to align, attach, and fit a dispensing unit is avoided. On the other hand, the danger of leaks is omitted which can result from connecting units not being attached correctly.

In the ampoule according to the invention, a sealed arrangement of the container with the chambers in the inner chamber or space of the housing can be guaranteed without any additional sealing elements solely by a tight contact of the walls of the container and the housing over an extended wall section. Thus, the discharge of the substances to be mixed can occur directly from the chambers of the container into the mixing chamber. Additional conduits or channels and/or cone sections to be sealingly inserted are avoided. These aspects are also true for the embodiment according to claim 10, with the function of the container according to claim 1 here being performed by the piston unit according to claim 10 and the function of the piston unit according to claim 1 being performed by the container of claim 10.

Prior to operation, according to the invention, the only manipulation requirement for the operator for putting the ampoule into operation is to open a sealing means at the front dispensing opening of the chambers. In one embodiment, a sealing foil laterally protruding from the housing is simply pulled off. This can occur by hand. In another embodiment the sealing foil is automatically pierced by housing protrusions when the container is pushed forward in the direction of the mixing chamber during the forward motion of the piston. In contrast to the hollow piercing needles known from prior art or to tubular coupling pieces having blades these housing protrusions do not form any through channels circumferentially sealed with respect to the foil but rather serve merely for perforating the foil.

In another embodiment the sealing means is a type of plug formed such that, for activating the ampoule during the forward motion of the chamber container in a direction towards the mixing chamber, said plug abuts the housing and, thereby, is pressed into the interior of the chamber whereby the plug clears the chamber dispensing opening. Here, the chamber container can be directly pressed against the housing by hand or indirectly by applying pressure onto the piston unit. Rather than separate plugs for each chamber, preferably, a common plug unit, for example a double plug is provided for a container having two chambers for substances.

BRIEF DESCRIPTION OF THE DRAWINGS

Preferred embodiments of the invention are described herein with reference to the following drawings:

FIG. 1 is a partial sectional elevation view of a first embodiment of the invention in a disassembled state;

FIG. 2 is a partial sectional view of the first embodiment according to FIG. 1 in an assembled state in which the substances of the chambers are stored in a sealed manner;

FIG. 3 is a sectional view of the first embodiment in an assembled state along a line 3—3 of FIG. 2;

FIG. 4 is a view of a sealing means used in the illustrated embodiment;

FIG. 5 is a partial sectional elevation view of a second embodiment according to the invention in a disassembled state;

FIG. 6 is a partial sectional view of the substance container in a closed state used in the second embodiment according to FIG. 5;

FIG. 7 is a sectional view along a section line 7—7 in FIG. 6 of a sealing means used in the second embodiment;

FIG. 8 is a partial sectional, broken away view of the second embodiment in an activated state;

FIG. 9 is a sectional, broken away view of essential parts of a third embodiment of the invention.

DETAILED DESCRIPTION OF THE PREFERRED EMBODIMENTS

Figure 10:
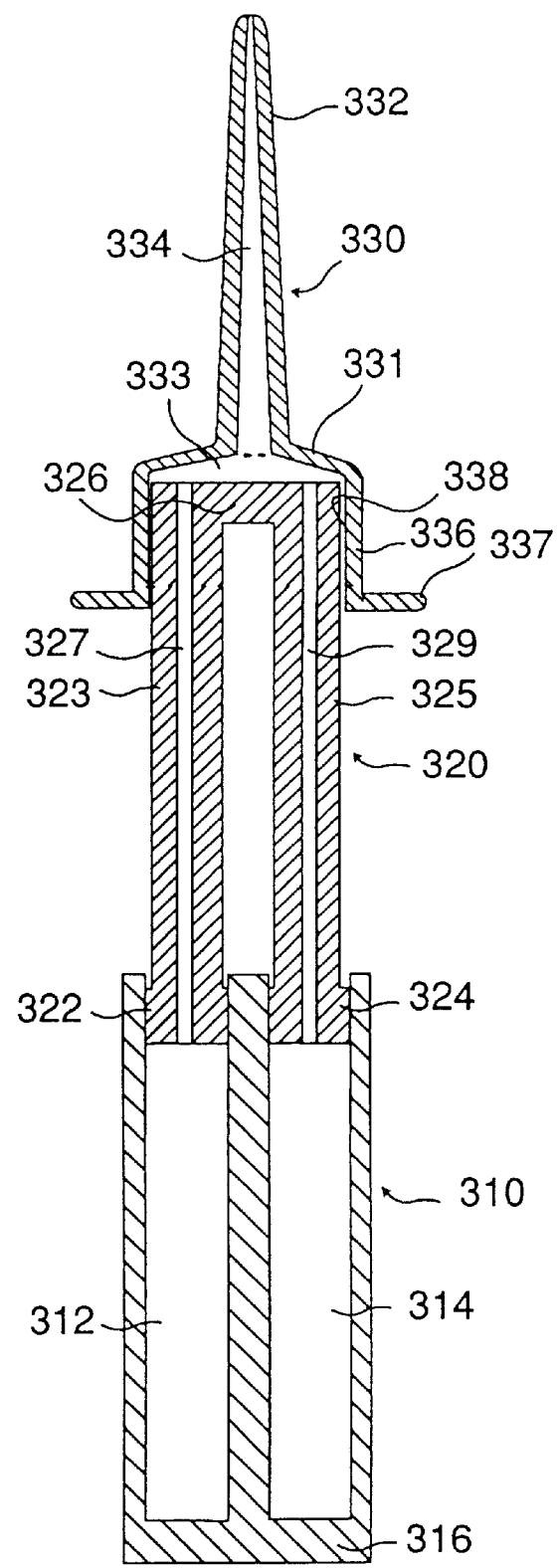
FIG. 10 is a sectional elevation of a fourth embodiment of the invention in an assembled state in which the substances are stored in the chambers in a sealed manner.

The first embodiment of a multi-chamber ampoule according to the invention, shown in FIGS. 1 through 4, comprises essentially three parts, namely a container 10, a piston arrangement 20, and a housing 30. Two separate cylindrical chambers 12 and 14 are formed in the container 10, which extend in the axial direction of the container 10 and which are open both on their rear (lower) end and on their front (upper) end.

The piston arrangement 20 comprises two circular cylindrical pistons 22 and 24 arranged parallel to one another at a distance, with their rear ends being connected to one another by means of a plate forming a piston unit 26. The pistons 22 and 24 are coaxially aligned with the chambers 12 and 14 and the exterior diameter of the pistons 22 and 24 essentially corresponds to the interior diameter of the circular cylindrical cross section of the chambers 12 and 14 such that the pistons 22 and 24 inserted into the chambers 12 and 14 contact the chamber walls as tight as possible, in particular, liquid tight, however, said pistons can still be displaced in the axial direction. In order to fulfill both said functions contradicting one another, the front ends 21 and 23 of the pistons 22 and 24 are slightly oversized with regard to the remaining length of the piston.

The housing 30 comprises a front section 32 and a rear section 36. The front section 32 has a tubular shape and surrounds a discharge channel 34 having a comparatively small circular cross section. The rear section 36 of the housing 30 has considerably larger lateral dimensions than the front section 32 and defines an inner chamber or space 38 which is open towards the rear and leads in a forward direction into the discharge channel 34. The inner chamber 38 is coaxially aligned with the container 10. The container 10 has, perpendicular to the axial direction, an outer cross-sectional area which essentially corresponds to the inner cross sectional area of the hollow chamber 38 so that the container 10, being inserted from the rear into the inner chamber 38, engages the circumferential wall of the housing 30, which defines the inner chamber 38, as tight as possible, in particular, liquid tight with its outer container wall. The housing 30 is provided with an essentially radially extending shoulder 31 between the small diameter of the tubular front section 32 and the comparably widened rear section 36 with its larger cross section dimensions. The shoulder defines a very flat space 33 in the form of a truncated cone constituting a transitional space between the wide inner chamber 38 and the relatively narrow exit channel 34, also called discharge or mixing chamber.

The shoulder 31 is sloped or beveled according to FIGS. 1 and 2 and offers an engaging surface for acting finger pressure thereupon. Another finger of the same hand is able to press the piston arrangement, so that the piston arrangement and the housing can be slidingly moved together in a telescope-like fashion in order to dispense the mixture.

In addition, in FIG. 1 a sealing means 40 is shown which is shown in FIG. 4 from above and which is provided with two sealing sections 42 and 44 and a pull-off section 46.

FIGS. 2 and 3 show the embodiment of the multi-chamber ampoule according to the invention in a state in which the ampoule can be shipped or stored, otherwise being immediately ready for operation, however. In the storing or shipping state shown in FIGS. 2 and 3 the front end of the chambers 12 and 14 are closed and sealed with the sealing element 40, respectively. The sealing element 40 can be a foil, for instance, which is glued to the front surface of the container 10 and which is preferably welded to the front surface in the form of a plastic foil or a corresponding plastic coating. For this purpose, hot sealing processes sufficiently known from plastic technology and the like can be used. The rear end of the chambers 12 and 14 is closed and sealed by the pistons 22 and 24 with the front ends 21 and 23 of the pistons being inserted over a certain distance into the chambers 12 and 14, which distance is short in relation to the length of the chambers 12, 14. The sealing means 40 and the pistons 22 and 24 define a fluid and liquid tight space or chamber within the chambers 12 and 14, respectively. The substances 52 and 54 are contained in these spaces to be mixed with one another during discharge.

In the first embodiment as shown in FIG. 3 and indicated in dashed lines in FIG. 1, a slot-shaped cut out 35 is provided in a side wall of the rear section 36 of the housing 30 through which cut out the pull-off section 46 of the sealing means 40 is extended outward. This measure allows that, for a common application of the substances and for putting the multi-chamber ampoule into use, the sealing means 40 can be pulled off from the ampoule in the assembled state shown in FIGS. 2 and 3, thus clearing the upper openings 13 and 15 of the chambers 12 and 14. In this connection it must be taken into account that the foil used as a sealing means 40 is thin to such an extent that during and after removal of the foil through the cut out 35 no considerable leaks open between the outer wall of the container 10 and the wall of the rear section 36 of the housing surrounding the inner space 38. Additionally, the front section of the container 10 is tightly pressed against the inner wall of the housing 30, which tapers towards the front in the region of the shoulder 31, by means of the pressure exerted on the piston arrangement 20 necessary for the activation. Therefore, the front end of the container 10 tightly and securely seals the space 33 against lateral leaks such that the substances 52 and 54 exit from the front openings of the chambers 12 and 14 under the influence of the thrust of the piston arrangement 20, arrive via the space 33 in the discharge channel 34 and exit at the front end thereof. Here, the two substances 52 and 54 are mixed with one another in the space 33 and in the discharge channel 34. The mixing effect can be enhanced such that a static mixing element (not shown) is provided in the discharge channel 34. Such mixing elements are generally known and can have the form of a spiral, for example.

The sealing means 40 can also be used in an embodiment not having a pull-off section 46. Then the sections 42 and 44 would be provided and designed such that they are forced away by applying a pressure force to the piston arrangement 20 and thereby exposing the front openings 13 and 15 of the chambers 12 and 14. The sealing means 40 can also be provided in the form of a thin skin or membrane integrated in the container 10 and bursting when being exposed to pressure. Furthermore, sharp protrusions extending backwards can be provided on the inner wall of the shoulder 31 which protrusions pierce the skin or membrane which spans over the upper openings 13 and 15 of the chambers 12 and 14 when pressure is applied to the piston arrangement 20 in the forward direction. For this embodiment, it is advantageous when the container 10 is slidingly arranged in the housing 30 such that it moves forward when a pressure force is applied to the piston arrangement and, thus, the skin or membrane is moved into the sharp protrusions. Alternatively, opening or piercing of the skin can also be achieved by directly applying pressure to the container 10. When such or other sealing means without a pull-off section 46 are used the cut out 35 is omitted.

The parts 10, 20, and 30 of the multi-chamber ampoule are preferably made from a thermoplastic material, for example, polyethylene. Here, the piston arrangement 20 can be made from a plastic material of greater hardness, however, the container 10 and the housing 30 as well should exhibit a certain elasticity.

The second embodiment of a multi-chamber ampoule according to the invention, shown in FIGS. 5 through 8, comprises essentially three parts, namely a container 110, a piston arrangement 120, and a housing 130, like in the first embodiment. Two separate cylindrical chambers 112 and 114 are formed in the container 110, extending in the axial direction of the container 110 and being open both at their front end and also at their rear ends. At the bottom end of the container 110 a radially outwardly extending section 116 is provided.

The piston arrangement 120 comprises two separate pistons 122 and 124 having a circular cylindrical shape, as well as two piston rods 123 and 125 positioned parallel at a distance from one another, with their ends being connected to one another by means of a plate 126. The outer diameter of the pistons 122 and 124 essentially corresponds to the inner diameter of the circular cylindrical cross section of the chambers 112 and 114, such that the pistons 122 and 124 inserted into the chambers 112 and 114 contact or engage the chamber walls as tight as possible, in particularly liquid tight, however, are still displaceable in axial direction. For this purpose, the pistons 122 and 124 can be slightly oversized with regard to the cross section of the chambers 112 and 114.

The housing 130 of the second embodiment is essentially formed in the same manner as the housing 30 of the first embodiment. Therefore, in FIG. 4, corresponding housing parts are provided with reference numbers each having a "1" preceding those shown in FIG. 1. Since in the housing 130 a different sealing means 140 is provided, the cut out 35 provided in certain embodiments of the housing 30 is also omitted in the second embodiment. For the purpose of better handling, a radially outwardly extending section 137 is additionally formed at the rear end of the housing 130.

The sealing means 140 is provided in the form of a plug in order to tightly seal the upper openings 113 and 115 of the chambers 112 and 114. The sealing means comprises a plate 142 with its exterior lateral dimensions essentially correspond to those of the container 110 and to the lateral dimensions of the inner chamber 138, respectively. Two semi-circular through holes 143 are provided in the plate 142. Adjacent to the through holes 143, two legs 144 protrude from the bottom of the plate in a downward direction which legs have a semicircular cross section and each leg leads into a cylindrical plug 146 at its lower end. The plugs 146 serve to seal the upper openings 113 and 115 in a fluid-tight manner and, therefore, they have an appropriately dimensioned outer diameter in comparison to the inner diameter of the openings 113 and 115.

FIG. 6 shows the container 110 in a ready-to-use state. In this state, the upper openings 113 and 115 of the chambers 112 and 114 are fluid tightly sealed by the plugs 146 of the sealing means 140. The bottom end of the chambers 112 and 114 is closed by the pistons 122 and 124 inserted therein. Therefore, the sealing means 140 and the pistons 122 and 124 each define a fluid or liquid tight space inside the chambers 112 and 114. In these spaces or chambers, the substances (not shown) to be mixed with one another during discharge are contained.

The ready-to-use container 110 shown in FIG. 6 can be stored and transported separately from the housing 130. However, the second embodiment of the invention shown in FIGS. 5 through 8 is also preferably stored and transported in such a state in which the ready-to-use container 110 is already inserted into the inner space 138 of the housing 130, but only to such an extent that the sealing means 140 is still at a distance from the shoulder 131 or only slightly engages the shoulder 131. Thus, the multi-chamber ampoule is not yet in an activated state.

Immediately prior to putting the multi-chamber ampoule into use the activation occurs such that by completely inserting the container 110 into the inner space 138 of the housing 130 the sealing means 140 is pressed against the shoulder 131 which causes the plugs 146 to move inwardly from the openings 113 and 115 into the chambers 112 and 114 and the plate 142 comes into contact with the upper front surface of the container 110 as shown in FIG. 8. Since the chambers 112 and 114 have a larger inside diameter than the openings 113 and 115 and the outer diameter of the plug 146 is smaller than the inside diameter of the chambers 112 and 114 below the openings 113 and 115, respectively, the upper ends of the chambers 112 and 114 are no longer sealed and the substances contained therein can flow into the discharge or mixing space 131 through the openings 113 and 115 as well as the through holes 143, which are now directly adjoining. The section 116 formed at the rear end of the container 110 serves to facilitate the activation by fingers with other fingers of the same hand acting upon the section 137 or the shoulder 131 of the housing 130. It is obvious for one skilled in the art that the sections 116 and 137 can be embodied in many different forms in order to achieve the desired function, for example, also in the form of a protrusion provided only at one point of the respective circumferential wall or in the form of two opposite protrusions.

Then, in the activated state, the pistons 122 and 124 are moved forward by means of the piston rods 123 and 125, connected to one another by means of the plate 126, into the chambers 112 and 114 in order to dispense the substances. Thereby, the substances are pressed into the discharge chamber or space 133 and dispensed from here via the discharge channel 134, as indicated by the arrows shown in FIG. 8.

In the discharge channel 134 a static mixer (not shown) can optionally be provided, like in the first exemplary embodiment. As in the first embodiment, instead of separate pistons 122 and 124 and corresponding piston rods 123 and 124 a one-piece piston arrangement can be used as that of the first embodiment. In the first embodiment, separate pistons with corresponding piston rods can likewise be used.

The shown sealing means 140 has the advantage that, in the state shown in FIG. 8 after the activation, the plate 142 clamped between the upper front side of the container 110 and the bottom of the shoulder 131 ensures that the plugs 146 cannot seal the openings 113 and 115 any more when the pistons 122 and 124 are moved forward since they are kept at a distance from the openings 113 and 115 by means of the legs 144. Simultaneously, the plate 142 can enhance the sealing between the exterior wall of the container 110 and the interior wall of the housing 130. For this purpose, the sealing means 140 can be made from a rubber-like material.

It is obvious for one skilled in the art that the sealing means 140 could be modified in many ways. This is particularly true for the geometry of the plate 142, the through holes 143, and the legs 144. Regarding the material for the individual parts of the second embodiment reference is made e.g. to the materials of the first embodiment.

Essential parts of the third embodiment are shown in FIG. 9. Here, the chambers 212 and 214 of the container 210 are closed at their upper end by means of a skin or membrane 240. A sharp protrusion 239 is provided inside the housing 230. In order to activate it, the container 210 is pushed upwards in the direction towards the sharp protrusion 239 passing over a lip 235 extending radially inward. In doing so, the protrusion 239 pierces the membrane 240 such that the substance contained in the chambers of the container can be dispensed by means of a piston arrangement not shown. In the activated state, the lip 235 supports the sealing and, simultaneously, serves to prevent a displacement of the container 210 backwards due to pressure built-up during the forward motion of the piston arrangement.

It is obvious for one skilled in the art that similar means like the lip 235 can be provided in the first and second exemplary embodiment as well in order to enhance the sealing of the discharge or mixing chambers 33 and 133 and, in particular, to prevent a reverse motion of the containers 10 and 110 due to pressure development in the chambers 33 and 133. For this purpose, it is generally sufficient to provide a circular bead radially protruding inwardly from the inner wall of the housing 130 or to provide a circular bead radially protruding outwardly from the outer wall of the container 210. If necessary, locking means can be provided as well.

The fourth embodiment of a multi-chamber ampoule according to the invention shown in FIG. 10 comprises essentially three parts as well, namely a container 310, a piston arrangement 320, and a housing 330. In the container 310 two separate cylindrical chambers 312 and 314 are formed extending in the axial direction of the container 310 and being closed in their rear end by means of a bottom 316.

The piston arrangement 320 comprises two circular cylindrical pistons 323 and 325 provided in parallel to one another at a distance with their front ends being fixed to one another by means of a plate 326 forming the piston arrangement 320. The pistons are coaxially aligned with the chambers 312 and 314 and the outer diameters of the rear piston ends 322 and 324 is essentially correspond to the inner diameter of the circular cylindrical cross section of the chambers 312 and 314 such that the pistons inserted into the chambers 312 and 314 engage the chamber walls as tightly as possible, in particularly liquid tight, though still being shiftable in the axial direction. In order to fulfill both of the contradicting functions the rear ends 322 and 324 of the pistons can be slightly oversized in comparison to the remaining length of the pistons 323 and 325. The pistons 323 and 325 are each interspersed in their longitudinal direction by a through channel 327 and 329.

The housing 330 showing a discharge and mixing device comprises a front section 332 and a rear section 336. The front section 332 is provided in tubular form and surrounds a discharge channel 334 with a relatively small circular cross section. The rear section 336 of the housing 330 has substantially larger lateral dimensions than the front section 332 and defines an inner chamber 338 which is open to the rear and leads into the discharge channel 334 in the forward direction. The inner space or chamber 338 is coaxially aligned with the piston unit 320. The piston unit 320 has, transverse to the axial direction, an outer cross sectional area which is essentially identical to the inner cross sectional area of the hollow space 338 so that the piston unit 320, inserted from the rear into the inner chamber 338, closely engages with its outer wall the circumferential wall of the housing 330 which defines the inner space 338 and, particularly engages this wall liquid tight. Between the tubular front section 332, having a small diameter, and the rear section 336 which, in relation thereto is widened and has larger cross sectional dimensions, the housing 330 is provided with a shoulder 331 essentially extending in a radial direction and defining a very flat, truncated space 333 that constitutes a transitional space between the wide inner space 338 and the relatively narrow discharge channel 334. This space 333 is also called discharge or mixing space or chamber.

According to FIG. 10, the shoulder 331 is sloped. It provides a pressure contact surface for a finger and, with another finger of the same hand, it is possible to urge the container 310 such that the multi-chamber ampoule telescopically moves together for dispensing the mixture. In order to facilitate the telescoping movement the housing 330 is preferably provided with an extending section 337 corresponding to the extending section 137. Instead of an extension, grip wings extending obliquely downwards could be provided as well.

The sealing means for the longitudinal channels 327 and 329 of the pistons 323 and 325 are not shown in FIG. 10. The sealing means can be provided in the same manner as in the above-mentioned embodiments. However, in the embodiment according to FIG. 10, a sealing means can be provided at the rear end of the piston unit 320 such, for example, in the form of a skin or membrane covering the longitudinal channels and rupturing under the influence of pressure.

In the embodiment according to FIG. 10, a static mixer and means corresponding to the lip 235 of FIG. 9 can be provided in the housing 330 as well.

What is claimed is:

1. A multi-chamber ampoule for dispensing a mixture comprising several substances, including:
    a container (10; 110; 210) having a rear end and a frontal end;
    at least two substance chambers (12, 14; 112, 114; 212, 214) formed through said container (10; 110; 120), each of said at least two substance chambers (12, 14; 112, 114; 212, 214) being positioned parallel to one another and extending in an axial direction of the container (10; 110; 210) from said rear end to said frontal end of the container (10; 110; 210);
    at least two pistons (22, 24; 122, 124), each of said pistons slidingly inserted into one of said substance chambers (12, 14; 112, 114; 212, 214) in the axial direction through said container rear end and sealingly engaging an inner wall of the substance chamber (12, 14; 112, 114; 212, 214) receiving the piston (22, 24; 122, 124);
    sealing means (40; 140; 240) sealing said substance chambers (12, 14; 112, 114; 212, 214) at said frontal end of said container (10; 110; 210); and
    a housing (30; 130; 230) having a front section (32; 132) and a rear section (36; 136) adjacent to the front section (32; 132), said front section (32; 132) defining a discharge channel (34; 134), and said rear section (36; 136) defining an inner cavity (38; 138) in fluid communication with said discharge channel (34; 134), said inner cavity (38; 138) receiving said frontal end of said container (10; 110; 210) and having inner walls sealingly engaging said container (10; 110; 210) to define a mixing chamber (33; 133) within said inner cavity (38; 138) and in fluid communication with the discharge channel (34; 134), wherein, in a ready-to-use state of the multi-chamber ampoule, a substance (52, 54) can be contained within each substance chamber (12, 14; 112, 114; 212, 214) closed by the sealing means (40; 140; 240) and the pistons (22, 24; 122, 124), and upon breaching said sealing means (40; 140; 240), the substances exit said substance chambers (12, 14; 112, 114; 212, 214) directly into said mixing chamber (33; 133).

2. The multi-chamber ampoule according to claim 1, wherein, said sealing means is breached by the substances upon urging said pistons forwardly toward the frontal end of the container in order to dispense the substances into said mixing chamber to form a mixture which is dispensed to the exterior via the common discharge channel (32; 132).

3. The multi-chamber ampoule according to claim 1, in which a shoulder (31; 131) extends between the front section (32; 132) and the rear section (36; 136) of the housing (30; 130).

4. The multi-chamber ampoule according to claim 1, wherein a slot (35) is provided in a side wall of the housing (30) which provides access to said sealing means (40) for removing the sealing means (40).

5. The multi-chamber ampoule according to claim 1, wherein a sharp protrusion (239) for piercing the sealing means (240) is provided in the housing (230).

6. The multi-chamber ampoule according to claim 1, wherein the sealing means (40) is a peelable foil.

7. The multi-chamber ampoule according to claim 1, wherein the sealing means (240) is a skin which can be perforated.

8. The multi-chamber ampoule according to claim 1, wherein the sealing means (140) is a plug that can be urged into the chamber (112, 114).

9. The multi-chamber ampoule according to claim 1, wherein the pistons (20, 22) are connected to one another at their rear end forming a one-piece piston arrangement (20).

10. The multi-chamber ampoule according to claim 1, wherein a circular bead (235) is formed on one of the interior wall of the housing (230) and the exterior wall of the container.

11. A multi-chamber ampoule for dispensing a mixture having one or more substances comprising:
    a container (310) having a rear end and a frontal end;
    at least two substance chambers (312, 314) formed through said container (310), said substance chambers (312, 314) being positioned parallel to one another and extending in an axial direction of the container (310) from said rear end to said frontal end of the container, said substance chambers (312, 314) being closed at said rear end by a bottom (316);
    a piston (322, 323, 324, 325) slidingly and sealingly inserted in an axial direction in each of said substance chambers (312, 314), each of said pistons (32, 323, 324, 325 having a through channel (327, 329) formed therethrough in the axial direction, and said pistons (322, 323, 324, 325) are fixed to one another forming a piston unit (320);
    a housing (330) having a front section (332) and a rear section (336) adjacent to the front section, said front section defining a discharge tunnel (334), and said rear section having an inner cavity (338) provided therein in fluid communication with said discharge tunnel (334), said inner cavity receiving at least a portion of said piston unit (320) such that the piston unit (320) defines and tightly seals a mixing space (333) inside the housing (330); and
    sealing means closing said through channels (327, 329) opening into said mixing space, wherein, in the ready-to-use state of the multi-chamber ampoule, one end of the chambers (312, 314) is closed by the piston unit (320), and the through channels (327, 392) of the pistons (322, 323, 324, 325) have one end open to the respective chamber (312, 314) and an opposing end closed by said sealing means, and upon breaching said sealing means, substances disposed in spaces defined by said chambers (312, 314) and through channels (327, 329) exit directly into said mixing space (333).

12. A multi-chamber ampoule for dispensing a mixture comprising several substances, including:

a container (10) having a rear end and a frontal end;

at least two substance chambers (12, 14) formed through said container (10), each of said substance chambers (12, 14) being positioned parallel to one another and extending in an axial direction of the container (10) from said rear end to said frontal end of the container, at least two pistons (22, 24), each of said pistons slidingly and sealingly inserted into one of said substance chambers (12, 14) in the axial direction;

sealing means (40) sealing said substance chambers (12, 14) at said frontal end of said container (10); and a housing (30) having a front section (32) and a rear section adjacent said front section, said front section (32) defining a discharge tunnel (34), and said rear section defining an inner cavity (38) in fluid communication with said discharge tunnel, said inner cavity (38) receiving said frontal end of said container (10) and having inner walls sealingly engaging said container (10) to define a mixing chamber (33) within said inner cavity (38), wherein, in a ready-to-use state of the multi-chamber ampoule, a substance (52, 54) can be contained in each substance chamber closed by the sealing means (40) and the pistons (22, 24), and upon breaching said sealing means (40), said substances exit said substance chambers (12, 14) directly into said mixing chamber (38), said housing including an engaging surface (31) for manually acting thereupon in order to slidingly move together said pistons and housing in a telescope-like manner for urging the substances out of said chambers (12, 14);

wherein said sealing means (40) is a peelable foil sealing said substance chambers (12, 14) from said mixing chamber (38) and said peelable foil includes a pull-off section (46) which extends through a slot (35) formed through wall of said housing (30) for removing the sealing means to allow said substances to breach said sealing means (40).

13. A multi-chamber ampoule for dispensing a mixture comprising several substances, including:

a container (110) having a rear end and a frontal end;

at least two substance chambers (112, 114) formed through said container (110), each of said substance chambers (112, 114) being positioned parallel to one another and extending in an axial direction of the container (110) from said rear end to said frontal end of the container, at least two pistons (122, 124), each of said pistons slidingly and sealingly inserted into one of said substance chambers (112, 114) in the axial direction;

sealing means (140) sealing said substance chambers (112, 114) at said frontal end of said container (110); and a housing (130) having a front section (132) and a rear section adjacent said front section, said front section (132) defining a discharge tunnel (134), and said rear section defining an inner cavity (138) in fluid communication with said discharge tunnel, said inner cavity (138) receiving said frontal end of said container (110) and having inner walls sealingly engaging said container (110) to define a mixing chamber (133) within said inner cavity (138), wherein, in a ready-to-use state of the multi-chamber ampoule, a substance can be contained in each substance chamber closed by the sealing means (140) and the pistons (122, 124), and upon breaching said sealing means (140), said substances exit said substance chambers (112, 114) directly into said mixing chamber (133), said housing including an engaging surface (131) for manually acting thereupon in order to slidingly move together said pistons and housing in a telescope-like manner for urging the substances out of said chambers (112, 114);

wherein said sealing means (140) is a plug means that, when activating the multi-chamber ampoule, abuts a housing wall (131) whereupon it is urged into said chambers (112, 114) clearing the upper ends thereof.

14. The multi-chamber ampoule according to claim 13, wherein said plug means (140) has plug sections (146) closing the upper ends of said chambers (112, 114) in the non-activated state of the multi-chamber ampoule, and a plate section (146) having through holes (143) and being provided at the plug means end opposite to the plug sections (146) for abutting against said housing wall (131) in the activated state of the multi-chamber ampoule and for assisting to seal said mixing chamber (133).

15. A multi-chamber ampoule for dispensing a mixture comprising several substances, including:

a container (210) having a rear end and a frontal end;

at least two substance chambers (212, 214) formed through said container (210), each of said substance chambers being positioned parallel to one another and extending in an axial direction of the container (210) from said rear end to said frontal end of the container, at least two pistons, each of said pistons slidingly and sealingly inserted into one of said substance chambers (212, 214) in the axial direction;

sealing means (240) sealing said substance chambers (212, 214) at said frontal end of said container (210); and a housing (230) having a front section and a rear section adjacent said front section, said front section defining a discharge tunnel, and said rear section defining an inner cavity in fluid communication with said discharge tunnel, said inner cavity receiving said frontal end of said container (210) and having inner walls sealingly engaging said container (210) to define a mixing chamber within said inner cavity, wherein, in a ready-to-use state of the multi-chamber ampoule, a substance can be contained in each substance chamber closed by the sealing means (240) and the pistons, and upon breaching said sealing means (240), said substances exit said substance chambers (212, 214) directly into said mixing chamber, said housing including an engaging surface for manually acting thereupon in order to slidingly move together said pistons and housing in a telescope-like manner for urging the substances out of said chambers (212, 214);

wherein said sealing means (240) is a skin at said upper ends of the chambers (212, 214) in the non-activated state of the multi-chamber ampoule and being perforated by means of a protrusion (239) in the activated state of the multi-chamber ampoule, said protrusion being provided within the mixing chamber of said housing (230).

* * * * *